(12) United States Patent
Trissel (10) Patent No.: US 10,085,681 B2
(45) Date of Patent: Oct. 2, 2018

(54) LANCING DEVICE WITH MOVING PIVOT DEPTH ADJUST

(71) Applicant: FACET TECHNOLOGIES, LLC, Kennesaw, GA (US)

(72) Inventor: John A. Trissel, Canton, GA (US)

(73) Assignee: FACET TECHNOLOGIES, LLC, Kennesaw, GA (US)

( * ) Notice: Subject to any disclaimer, the term of this patent is extended or adjusted under 35 U.S.C. 154(b) by 1054 days.

(21) Appl. No.: 13/859,969

(22) Filed: Apr. 10, 2013

(65) Prior Publication Data

US 2013/0274777 A1    Oct. 17, 2013

Related U.S. Application Data

(60) Provisional application No. 61/622,570, filed on Apr. 11, 2012.

(51) Int. Cl.
*A61B 17/32* (2006.01)
*A61B 5/151* (2006.01)
*A61B 5/15* (2006.01)

(52) U.S. Cl.
CPC ........ *A61B 5/15126* (2013.01); *A61B 5/1519* (2013.01); *A61B 5/150022* (2013.01); *A61B 5/15113* (2013.01); *A61B 5/15117* (2013.01); *A61B 5/15194* (2013.01); *A61B 5/150198* (2013.01); *A61B 5/15019* (2013.01); *A61B 5/150412* (2013.01); *A61B 5/150519* (2013.01)

(58) Field of Classification Search
CPC ............ A61B 5/1411; A61B 5/150022; A61B 5/15019; A61B 5/150412; A61B 5/150519; A61B 5/15113; A61B 5/15117; A61B 5/1519; A61B 5/15194; A61B 5/15126; A61M 37/0076; A01K 11/005

USPC ............................................ 606/172; 30/162
See application file for complete search history.

(56) References Cited

U.S. PATENT DOCUMENTS

| 4,787,398 A | 11/1988 | Garcia et al. |
| 4,823,806 A | 4/1989 | Bajada |
| 4,895,147 A | 1/1990 | Bodicky et al. |
| 4,924,879 A | 5/1990 | O'Brien |

(Continued)

FOREIGN PATENT DOCUMENTS

| DE | 10057832 C1 | 2/2002 |
| EP | 1764037 A1 | 3/2007 |

(Continued)

OTHER PUBLICATIONS

International Search Report and Written Opinion for PCT/US2013/035917; dated Sep. 6, 2013; 16 pgs.

*Primary Examiner* — Diane Yabut
*Assistant Examiner* — Erich Herbermann
(74) *Attorney, Agent, or Firm* — Gardner Groff Greenwald & Villanueva, PC (57) ABSTRACT

A depth-control mechanism for selectively-adjusting a lancing stroke depth of a lancet carrier. The depth-control mechanism includes a positioning tab that is configured to be repositioned along an axis that is orthogonal to the lancing stroke axis of the lancet carrier. The depth-adjustment mechanism also includes a tether that is pivotally coupled between the positioning tab and the lancet carrier. The positioning tab is configured to manipulate a pivot axis of the tether to adjust the lancing stroke length of the lancet carrier.

15 Claims, 11 Drawing Sheets

(56) References Cited

U.S. PATENT DOCUMENTS

| | | |
|---|---|---|
| 4,976,724 A | 12/1990 | Nieto et al. |
| 5,196,025 A | 3/1993 | Ranalletta et al. |
| 5,279,294 A | 1/1994 | Anderson et al. |
| 5,282,822 A | 2/1994 | Macors et al. |
| 5,318,583 A | 6/1994 | Rabenau et al. |
| 5,318,584 A | 6/1994 | Lange et al. |
| 5,423,847 A | 6/1995 | Strong et al. |
| 5,464,418 A | 11/1995 | Schraga |
| 5,554,166 A | 9/1996 | Lange et al. |
| 5,613,978 A | 3/1997 | Harding |
| 5,628,764 A | 5/1997 | Schraga |
| 5,730,753 A | 3/1998 | Morita |
| 5,741,288 A | 4/1998 | Rife |
| RE35,803 E | 5/1998 | Lange et al. |
| 5,871,494 A | 2/1999 | Simons et al. |
| 5,916,230 A | 6/1999 | Brenneman et al. |
| 5,951,492 A | 9/1999 | Douglas et al. |
| 5,954,738 A | 9/1999 | LeVaughn et al. |
| 5,984,940 A | 11/1999 | Davis et al. |
| 6,022,366 A | 2/2000 | Schraga |
| 6,045,567 A | 4/2000 | Taylor et al. |
| 6,099,484 A | 8/2000 | Douglas et al. |
| 6,156,050 A | 12/2000 | Davis et al. |
| 6,156,051 A | 12/2000 | Schraga |
| 6,168,606 B1 | 1/2001 | Levin et al. |
| 6,197,040 B1 | 3/2001 | LeVaughn et al. |
| 6,283,982 B1 | 9/2001 | LeVaughn et al. |
| 6,322,575 B1 | 11/2001 | Schraga |
| 6,332,871 B1 | 12/2001 | Douglas et al. |
| 6,409,740 B1 | 6/2002 | Kuhr et al. |
| 6,419,661 B1 | 7/2002 | Kuhr et al. |
| 6,451,040 B1 | 9/2002 | Purcell |
| 6,514,270 B1 | 2/2003 | Schraga |
| 6,530,937 B1 | 3/2003 | Schraga |
| 6,558,402 B1 | 5/2003 | Chelak et al. |
| 6,575,939 B1 | 6/2003 | Brunel |
| 6,602,268 B2 | 8/2003 | Kuhr et al. |
| 6,613,064 B2 | 9/2003 | Rutynowski et al. |
| 6,645,219 B2 | 11/2003 | Roe |
| 6,749,618 B2 | 6/2004 | LeVaughn et al. |
| 6,811,557 B2 | 11/2004 | Schraga |
| 6,852,119 B1 | 2/2005 | Abulhaj et al. |
| 6,887,253 B2 | 5/2005 | Schraga |
| 6,986,777 B2 | 1/2006 | Kim |
| 7,077,828 B2 | 7/2006 | Kuhr et al. |
| 7,105,006 B2 | 9/2006 | Schraga |
| 7,175,641 B1 | 2/2007 | Schraga |
| 7,223,276 B2 | 5/2007 | List et al. |
| 7,273,484 B2 | 9/2007 | Thoes et al. |
| 7,288,102 B2 | 10/2007 | Griffin et al. |
| 7,297,152 B2 | 11/2007 | Fukuzawa et al. |
| 7,311,718 B2 | 12/2007 | Schraga |
| 7,322,998 B2 | 1/2008 | Kuhr et al. |
| 7,452,366 B2 | 11/2008 | Chen et al. |
| 7,470,238 B2 | 12/2008 | Sakata et al. |
| 7,481,818 B2 | 1/2009 | Allen et al. |
| 7,510,564 B2 | 3/2009 | Mace |
| 7,621,931 B2 | 11/2009 | Schraga |
| 7,651,512 B2 | 1/2010 | Chelak et al. |
| 7,655,019 B2 | 2/2010 | LeVaughn et al. |
| 7,678,126 B2 | 3/2010 | Schraga |
| 7,678,127 B2 | 3/2010 | Trissel et al. |
| 7,682,318 B2 | 3/2010 | Alden et al. |
| 7,842,060 B2 | 11/2010 | List |
| 7,867,244 B2 | 1/2011 | Lathrop et al. |
| 7,883,473 B2 | 2/2011 | LeVaughn et al. |
| 7,905,898 B2 | 3/2011 | Schraga |
| 7,909,842 B2 | 3/2011 | Flynn et al. |
| 7,914,547 B2 | 3/2011 | Curry et al. |
| 7,947,057 B2 | 5/2011 | Schraga |
| 7,955,348 B2 | 6/2011 | Trissel et al. |
| 8,016,848 B2 | 9/2011 | Lathrop et al. |
| 8,043,318 B2 | 10/2011 | Schraga |
| 8,048,097 B2 | 11/2011 | Schraga |
| 8,105,347 B2 | 1/2012 | Schraga |
| 8,152,740 B2 | 4/2012 | Thoes et al. |
| 8,211,036 B2 | 7/2012 | Schraga |
| 8,257,380 B2 | 9/2012 | Schraga |
| 8,357,107 B2 | 1/2013 | Draudt et al. |
| 8,366,729 B2 | 2/2013 | LeVaughn et al. |
| 8,398,664 B2 | 3/2013 | Lamps et al. |
| 8,469,986 B2 | 6/2013 | Schraga |
| 2003/0088261 A1 | 5/2003 | Schraga |
| 2003/0212344 A1 | 11/2003 | Yuzhakov et al. |
| 2004/0039302 A1 | 2/2004 | Kim |
| 2004/0127818 A1 | 7/2004 | Roe et al. |
| 2004/0162573 A1 | 8/2004 | Kheiri |
| 2004/0186500 A1 | 9/2004 | Koike et al. |
| 2004/0249405 A1 | 12/2004 | Watanabe et al. |
| 2005/0125017 A1 | 6/2005 | Kudrna et al. |
| 2005/0125019 A1 | 6/2005 | Kudrna et al. |
| 2005/0159768 A1 | 7/2005 | Boehm et al. |
| 2005/0234492 A1 | 10/2005 | Tsai et al. |
| 2005/0234495 A1 | 10/2005 | Schraga |
| 2006/0095057 A1* | 5/2006 | Yi ............... A61B 17/3213 606/167 |
| 2006/0100655 A1 | 5/2006 | Leong et al. |
| 2006/0100656 A1 | 5/2006 | Olson et al. |
| 2006/0157362 A1 | 7/2006 | Schraga |
| 2006/0173478 A1 | 8/2006 | Schraga |
| 2006/0224172 A1 | 10/2006 | LeVaughn et al. |
| 2006/0241668 A1 | 10/2006 | Schraga |
| 2006/0247671 A1 | 11/2006 | LeVaughn |
| 2006/0264996 A1 | 11/2006 | LeVaughn et al. |
| 2007/0055298 A1 | 3/2007 | Uehata et al. |
| 2007/0083222 A1 | 4/2007 | Schraga |
| 2007/0100364 A1 | 5/2007 | Sansom |
| 2007/0173874 A1 | 7/2007 | Uschold et al. |
| 2007/0173875 A1 | 7/2007 | Uschold |
| 2008/0082117 A1 | 4/2008 | Rue |
| 2008/0146966 A1 | 6/2008 | LeVaughn et al. |
| 2008/0147108 A1 | 6/2008 | Kennedy |
| 2008/0255598 A1 | 10/2008 | LeVaughn et al. |
| 2008/0269639 A1* | 10/2008 | Korner ............ A61B 5/1411 600/583 |
| 2009/0030441 A1 | 1/2009 | Kudrna et al. |
| 2010/0160942 A1 | 6/2010 | Lamps et al. |
| 2010/0234870 A1 | 9/2010 | Ruf |
| 2010/0312266 A1* | 12/2010 | Fukuzawa ........ A61B 5/1411 606/185 |
| 2011/0313438 A1* | 12/2011 | Robbins .......... A61B 5/1411 606/172 |

FOREIGN PATENT DOCUMENTS

| | | |
|---|---|---|
| EP | 1779780 A2 | 5/2007 |
| EP | 1797822 A1 | 6/2007 |
| EP | 2221000 A1 | 8/2010 |
| WO | 03015627 A2 | 2/2003 |
| WO | 03070099 A1 | 8/2003 |
| WO | 03071940 A1 | 9/2003 |
| WO | 2006138634 A2 | 12/2006 |
| WO | 2009069720 A1 | 6/2009 |
| WO | 2010080584 A1 | 7/2010 |
| WO | 2011127346 A1 | 10/2011 |

* cited by examiner

LANCING DEVICE WITH MOVING PIVOT DEPTH ADJUST

CROSS-REFERENCE TO RELATED APPLICATION

This application claims the priority benefit of U.S. Provisional Patent Application Ser. No. 61/622,570 filed Apr. 11, 2012, the entirety of which is hereby incorporated herein by reference for all purposes.

TECHNICAL FIELD

The present invention relates generally to the field of medical devices, and more particularly to a lancing device for blood sampling and testing, and an incorporated mechanism for adjusting the penetration depth of the lancet tip.

BACKGROUND

Lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation.

A lancet is typically propelled by the drive mechanism from a retracted position within the housing to an extended position wherein a sharp tip portion of the lancet projects from the housing to prick the subject's skin at a desired lancing site. The lancet is typically a disposable component that is removably mounted into a receiver or lancet carrier portion of the drive mechanism of a lancing device. A used lancet typically is removed from the lancet carrier after sampling for subsequent disposal. An ejection mechanism can optionally be included for discharge of the used lancet from the lancing device. A new, sterile lancet is then replaced into the lancet carrier for further sampling.

A depth-control mechanism can optionally be provided to adjust the penetration depth of the lancet, to control sample size and/or to minimize pain. Known depth control mechanisms typically include endcaps that are adjustably positioned relative to the lancing device housing, and movable stops that limit the travel of the drive mechanism by contact with the lancet carrier.

Ongoing improvement to depth control mechanisms for lancing devices is sought. It is to the provision of improved lancing devices and lancing depth control mechanisms that the present invention is primarily directed.

SUMMARY

The present invention provides an improved lancing device with a depth control mechanism including a pivot post or column movably mounted within a pivoting link for adjustment of the lancet penetration depth. In example embodiments, adjustment of the lancing depth is controlled by varying the point of contact or connection of the pivot post to the lancing device housing, and/or by varying the length between the movable post relative to a stationary post and/or a spring retainer.

In one aspect, the present invention relates to a depth-control mechanism for selectively-adjusting a lancing stroke depth of a lancet carrier. The depth-control mechanism includes a positioning tab that is configured to be repositioned along an axis that is orthogonal to the lancing stroke axis of the lancet carrier. The depth-adjustment mechanism also includes a tether that is pivotally coupled between the positioning tab and the lancet carrier. The positioning tab is configured to manipulate an adjustable pivot axis of the tether to adjust the lancing stroke length of the lancet carrier.

In another aspect, the present invention relates to a depth-control mechanism for a lancing device including a drive-mechanism and a lancet carrier that is translationally secured along a lancing stroke axis within a housing including an engagement post and a proximal elongated aperture. The depth-control mechanism includes a repositioning post that is slidably secured along the housing proximal elongated aperture. The repositioning post is distance-adjustable relative to the engagement post. The depth-control mechanism also includes a link that couples the repositioning post and the lancet carrier. The link includes an elongate slot therein to slidably receive the repositioning post therein. The distance between the engagement post and the repositioning post is adjustable to control the penetration depth of the lancet carrier lancing stroke.

In still another aspect, the invention relates to a lancing device for carrying a lancet along a lancing stroke defining an axial direction. The lancing device includes a housing and a lancet carrier that is translationally mounted within the housing. The lancing device also includes a positioning slider that is translationally mounted with respect to the housing for movement in a transverse direction that is generally orthogonal to the lancing stroke axial direction. The lancing device also includes a pivotal linkage that is coupled between the positioning slider and the lancet carrier. Adjustment of the positioning slider varies the length of the lancing stroke.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIGS. 7A-12B are top views of the lancing device of FIG. 1 with portions of its external housing removed, showing the sequence of operation of the lancing device with the depth-adjust mechanism positioned at both the minimum and maximum settings.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
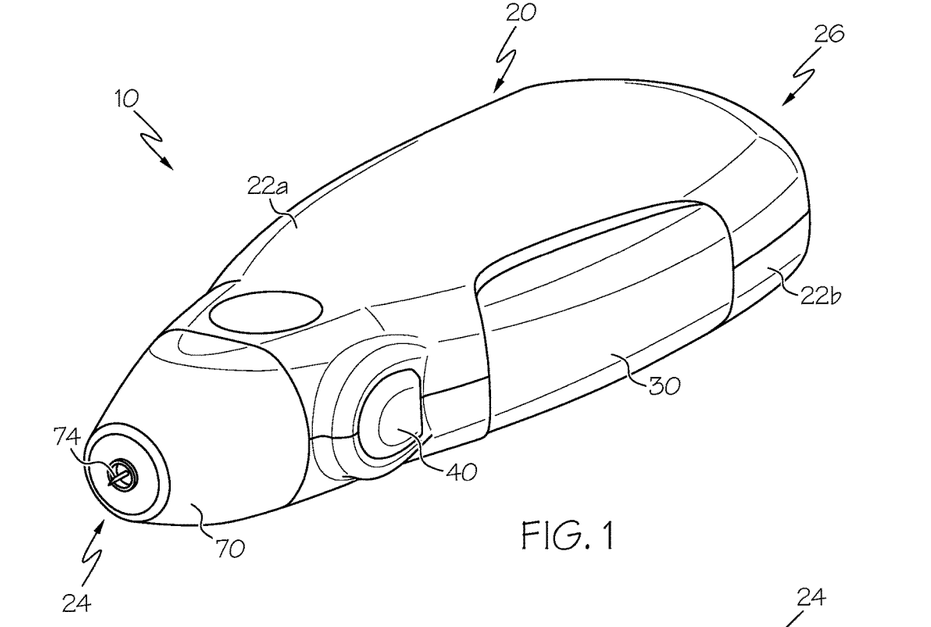
FIG. 1 is a front perspective view of a lancing device according to an example embodiment of the present invention.

With reference now to the drawing figures, wherein like reference numbers represent corresponding parts throughout the several views, FIGS. 1-13 show various aspects and features of a lancing device 10 according to an example form of the invention. As best shown in FIG. 1, the lancing device 10 includes a housing 20 generally comprising separable upper 22a and lower 22b housing shells, and a forward or distal end 24 defining a lancet opening through which at least a sharp tip 74 portion of a lancet 72 projects at the extended position of the lancing stroke to penetrate the skin of a subject during the lancing process. As best shown in FIGS. 3-13, the housing 20 protects a lancet carrier that is movably housed within the shells 22a, 22b. As depicted, the housing 20 has a generally elongate ergonomic shape that is wider at the back and tapering to a narrower front; however, alternate housing shapes can be utilized. The housing 20 can be constructed of a substantially rigid durable material, for example plastic, in example embodiments.

Figure 9A:
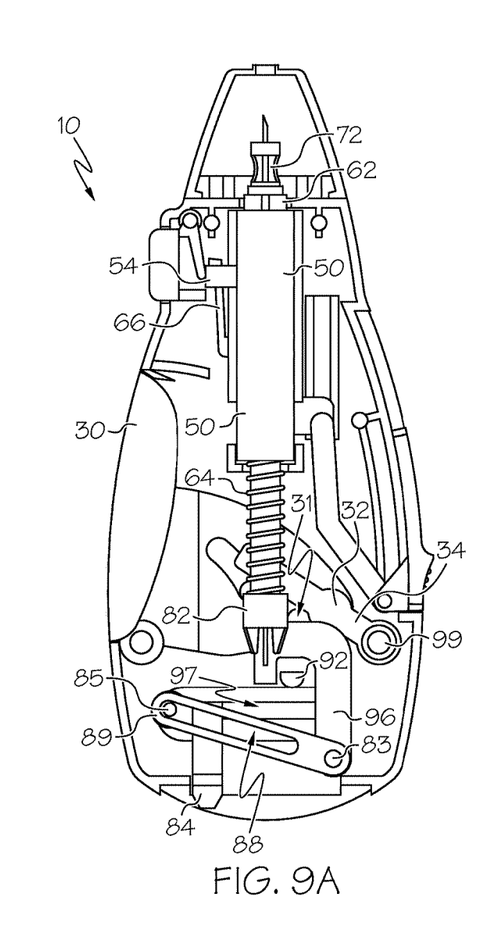
Figure 9B:
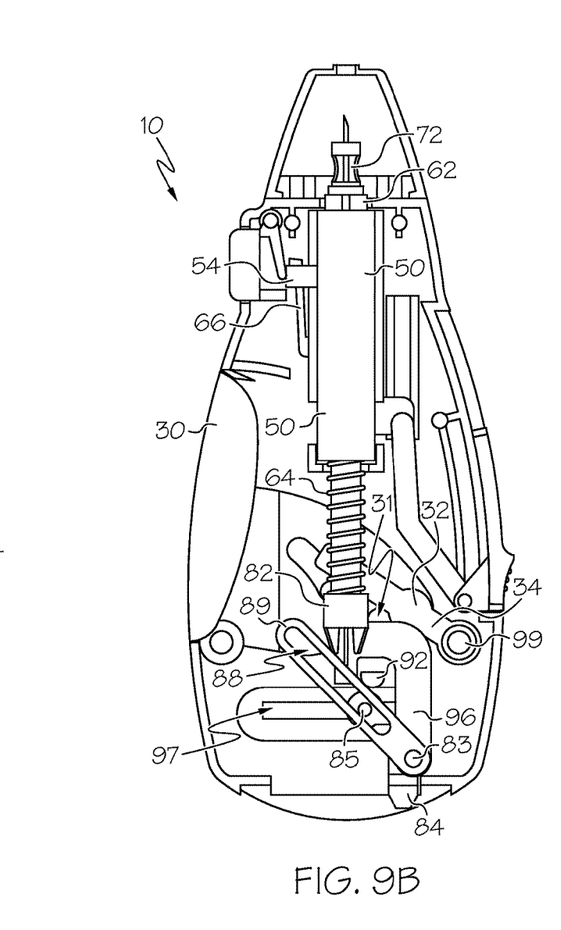
Figure 10A:
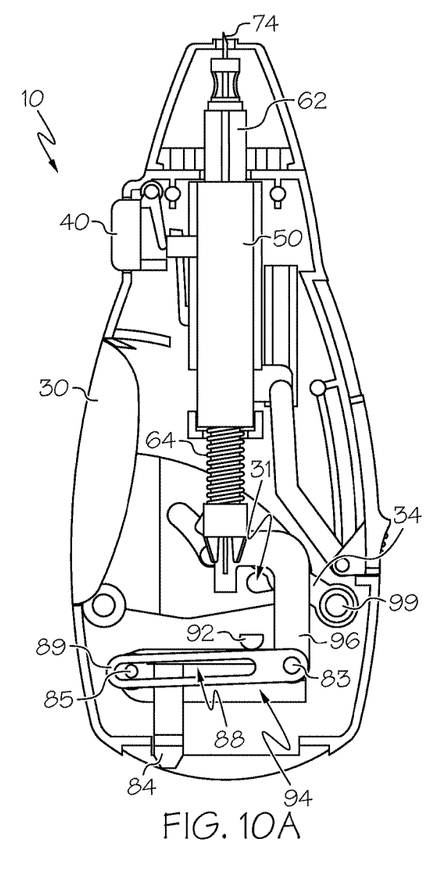
Figure 10B:
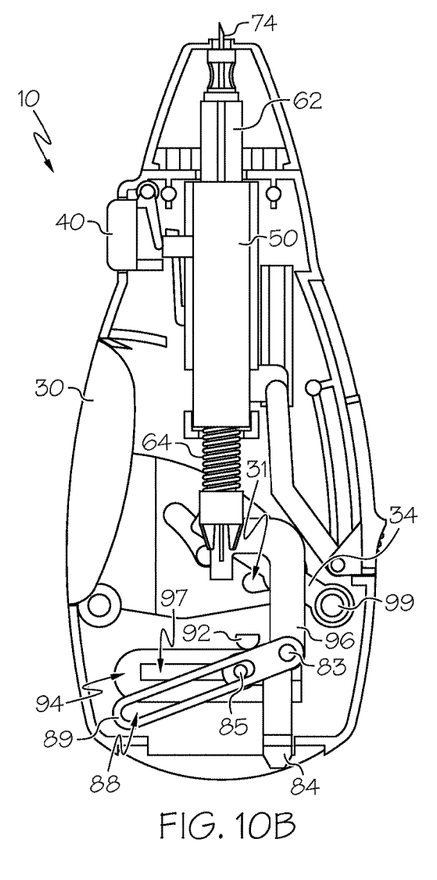

As best shown in FIGS. 9A-9B, a release button 40 projects through a side opening formed in the housing shells 22a, 22b. The release button 40 acts to release a trigger mechanism when depressed, thereby actuating the device to propel the lancet 72 along a lancing stroke from a retracted position within the housing 20 to an extended position. As best shown in FIGS. 10A-10B, the lancet 72 is in the extended position when at least the sharp tip portion 74 of the lancet projects outwardly of the lancet opening at the distal end of the housing 24.

A charging handle or actuator 30 forms a portion of, and is secured between, the housing shells 22a, 22b along one side of the housing 20. Actuating the charging handle or actuator 30 retracts the lancet carrier toward the housing proximal end 26 and energizes a biasing spring 64 to provide motive force to propel the lancet 72 along the lancing stroke.

Figure 13:
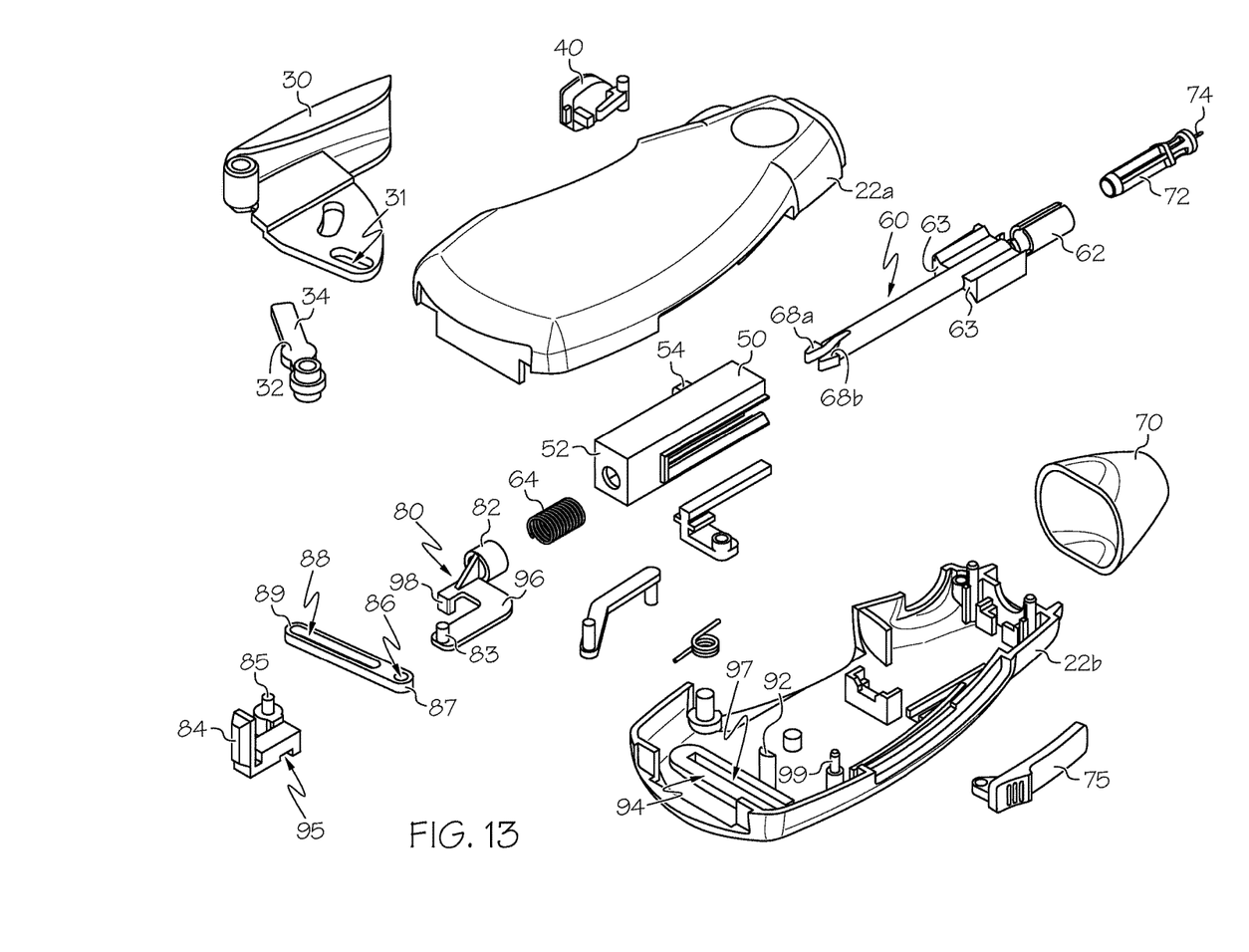
FIG. 13 is an exploded assembly view of the lancing device of FIG. 1.

As best shown in FIG. 13, the charging handle or actuator 30 includes a flange having at least one feature, for example a receiver aperture 31, to engage and/or actuate the drive mechanism. An arm 34 can be pivotally mounted to the housing 20 at a pivot end and have a free-end rod 32 movably mounted with respect to the flange feature. The pivot end can include a cylindrical receiver or sleeve. Actuating or pivoting the charging actuator 30 into the housing 20 forces the flange to move causing the arm 34 to pivot and engage a portion of a coupling or spring retainer 82, further retracting the lancet carrier and energizing the biasing spring 64. A further description of the charging mechanism is presented in Applicant's U.S. Provisional Patent Application No. 61/623,276 filed Apr. 12, 2013, and hereby incorporated by reference for all purposes.

Figure 2:
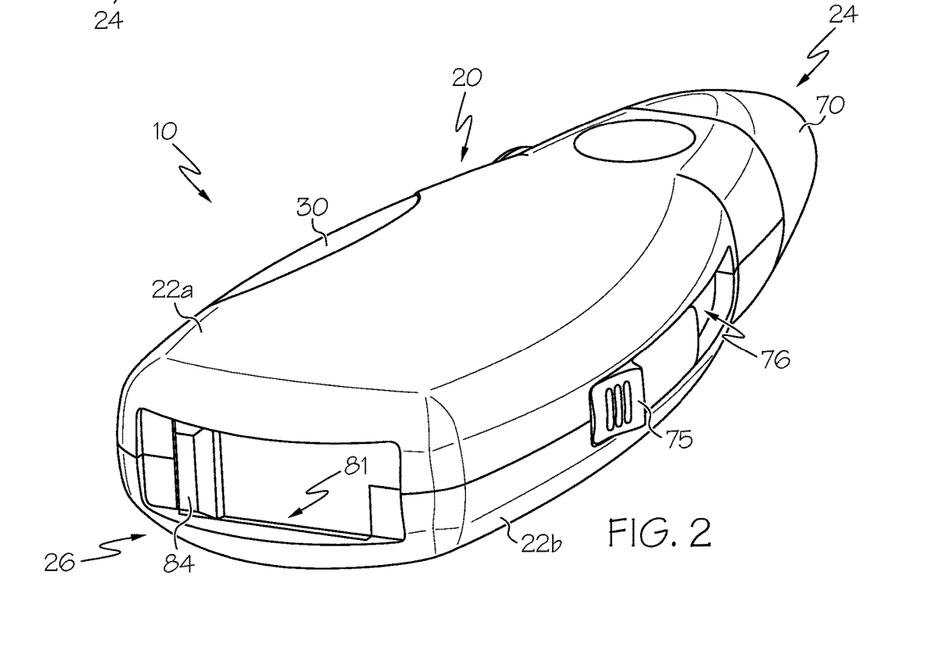
FIG. 2 is a rear perspective view of the lancing device of FIG. 1.

As depicted in FIG. 2, a proximal end 26 of the lancing device 10 includes an elongated opening 81 through which a depth positioning tab or slider 84 extends. As shown, the depth positioning tab 84 can be moved within the elongated limits of the opening 81. The positioning tab 84 and/or housing can include one or more interengaging surface features or couplings (not shown) for positioning the tab in discrete and/or infinitely variable positions within the opening 81 and allowing it to slide back and forth therein.

Figure 3:
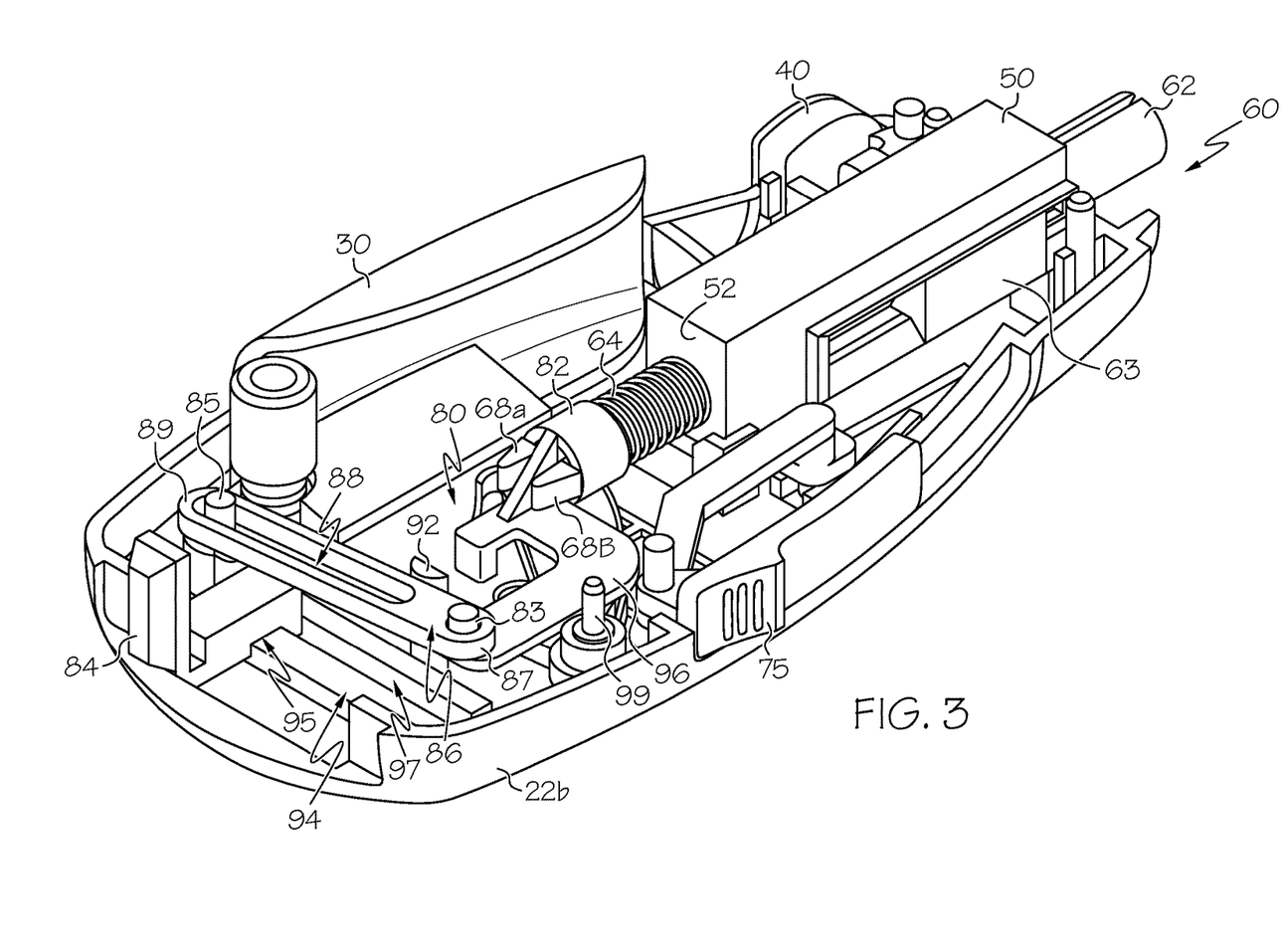
FIG. 3 shows the lancing device of FIG. 1 with portions of its external housing removed to show internal components thereof.
Figure 6:
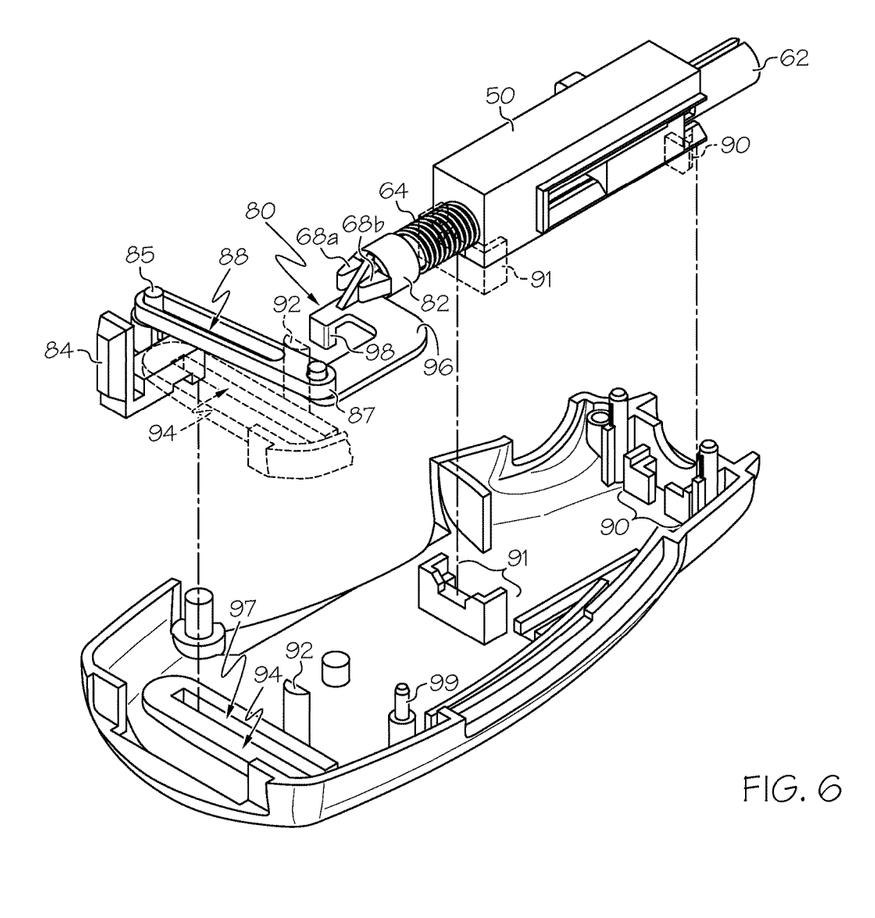
FIG. 6 is a partial assembly view of the lancing device of FIG. 1 with portions removed to show internal components thereof and with the depth-control mechanism at its minimum setting.

FIGS. 3 and 6 show the lancing device in a fixed position with its upper housing shell 22a removed. An inner drive core 50 is engaged within the housing 20 by one or more interengaging surface features in the lower housing shell 22b. In example embodiments, a portion of an inner drive mechanism is translationally mounted to slide within an axial bore or channel through the inner drive core 50. As depicted, the drive mechanism includes a lancet carrier 60 that has a distal collar or sleeve receiver 62 for releasably receiving the lancet 72. A biasing spring or combination drive-and-return spring 64 is engaged between a proximal wall 52 of the drive core 50 and a coupling or spring retainer 82. The biasing spring 64 propels the lancet 72 along the forward portion of the lancing stroke, and subsequently returns the lancet carrier to a retracted position within the housing 20 after the lancing has been completed. Optionally, separate drive and return springs can be used as desired. For example, an additional biasing spring can be added between a pair of arms 63 on the carrier 60 and the interior face of the proximal wall 52 to function as a drive spring, propelling the lancet 72 along the forward portion of the lancing stroke. A separate biasing spring 64 can function as a return spring, to return the lancet carrier 60 to a retracted position within the housing.

As depicted, the distal end of the lancet carrier 60 includes a split yoke having a pair of resilient forks 68a, 68b with outwardly-directed barbs to permit installation and retention of the biasing spring 64. The resilient forks 68a, 68b are inserted through an aperture in the proximal wall of the drive core 50. As best shown in FIG. 3, the resilient forks 68a, 68b can then insert through, and secure with a friction fit to, a coupling 82 at the distal end of a linkage joint or tether 80.

As best shown in FIGS. 9A-9B, a cantilevered release finger 66 projects from the axial shaft of the lancet carrier 60 for releasable engagement with a catch surface 54 of the drive core 50 to retain the lancet carrier 60 in its retracted position when the device is charged. When the release button 40 pressed, it contacts/depresses the release finger 66 to release the lancet carrier 60 to travel along its lancing stroke and thereby initiate the lancing procedure.

Figure 4:
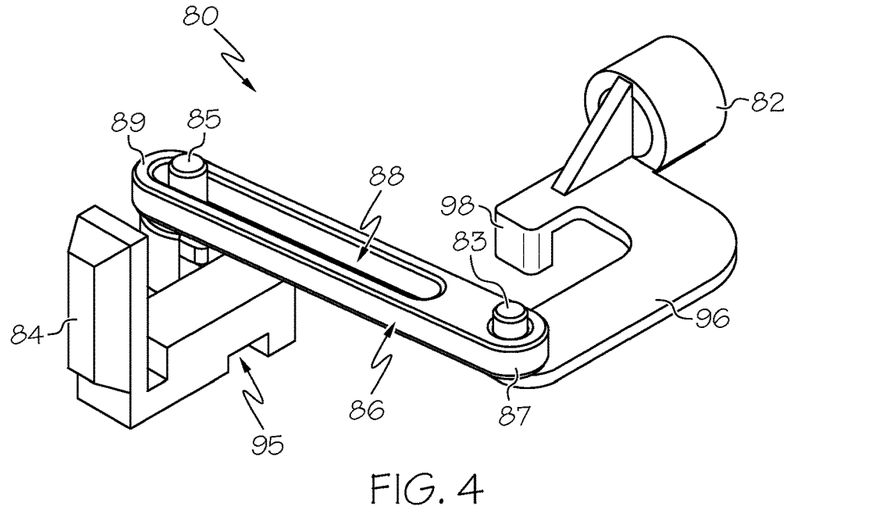
FIG. 4 is a top perspective view of the depth-control mechanism of the lancing device of FIG. 1.
Figure 5:
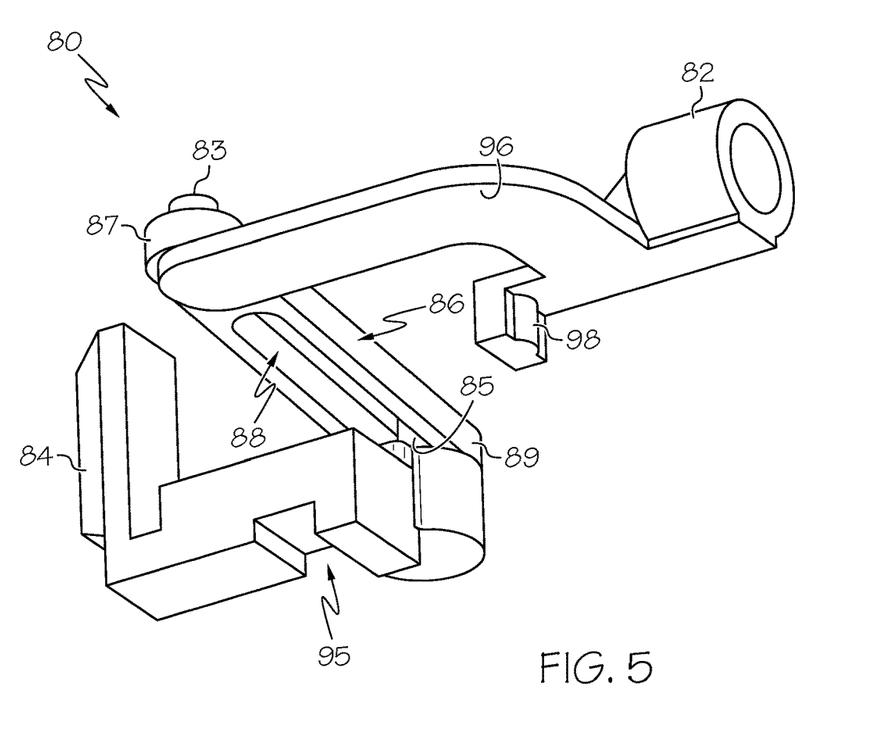
FIG. 5 is a bottom perspective view of the depth-control mechanism of the lancing device of FIG. 1.

FIGS. 4 and 5 show details of the linkage joint or tether 80 for adjustment of the penetration or lancing depth of the lancing stroke. In the depicted embodiment, the distal coupling 82 has an axially oriented bore or connector with a vertical divider at the proximal end to divide the flexible forks 68a, 68b secured within the coupling. The tether 80 has an elbow or hook-shaped arm 96 with a downwardly-extending grip 98 positioned directly proximal to the coupling 82, and an upwardly-extending post 83 at a laterally displaced end of the hook-shaped arm. The downwardly-extending grip 98 engages the arm 34. The upwardly-extending post 83 pivotally inserts through a pivot aperture 86 in a pivoting link. The pivoting link is slidably and pivotally connected between the positioning tab 84 and the tether 80. An elongated slot 88 extends between the pivot aperture 86 and a free end 89 of the link 86.

A pivot post 85 on the positioning tab 84 is received and slides within the link elongated slot 88. The positioning tab 84 has a downwardly-facing receiver channel and insert 95 to slidably engage a support guide 94 provided within the bottom housing shell 22b. The support guide 94 has an elongated channel 97 that extends horizontally across the bottom housing shell 22b. In use, the positioning tab insert 95 slidably inserts within the elongated channel 97.

FIG. 6 shows surface features of the bottom housing shell 22b engaging portions of the inner drive core 50 and the tether 80. As depicted by the dashed lines, interengaging surface features 90, 91 engage the proximal and distal ends of the inner drive core 50 in a fixed position within the bottom housing shell 22b. A proximal portion of the lower shell 22b includes an engagement post 92 for abutting the pivoting link 86 and functioning as a fulcrum about which the link 86 pivots. The engagement post 92 generally has an outer profile shaped to accommodate minimal surface contact with the pivoting link 86, for example a cylindrical or arcuate outer profile facing toward the proximal opening 81 in the housing 20. Optionally, the post can include other profiles as desired, for example, an angled or polygonal outer profile to define discrete surfaces along the contour of the outer profile. The bottom housing shell 22b can also have a pivot post 99 to pivotally receive the arm 34 pivot end.

Figure 7A:
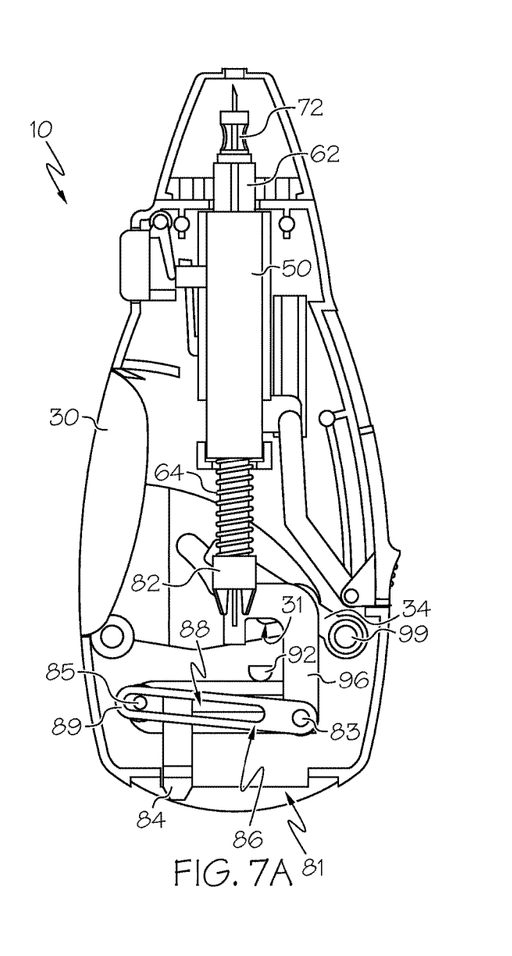
Figure 7B:
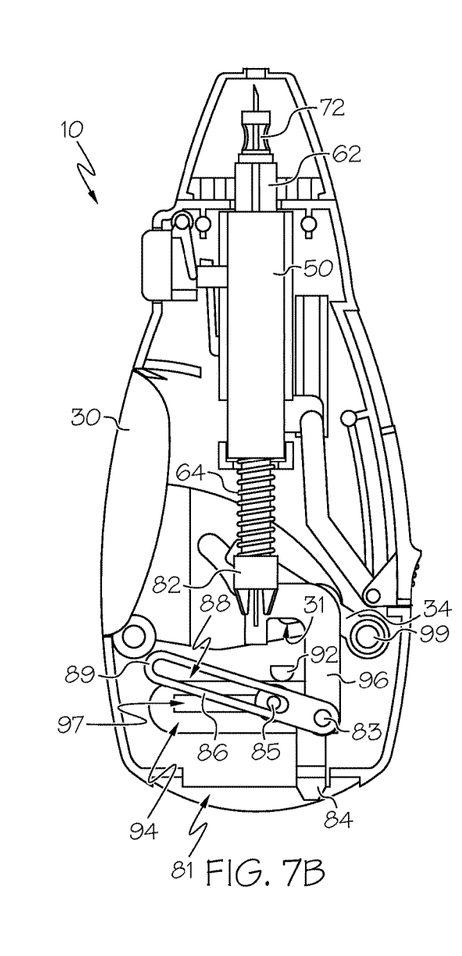
Figure 8A:
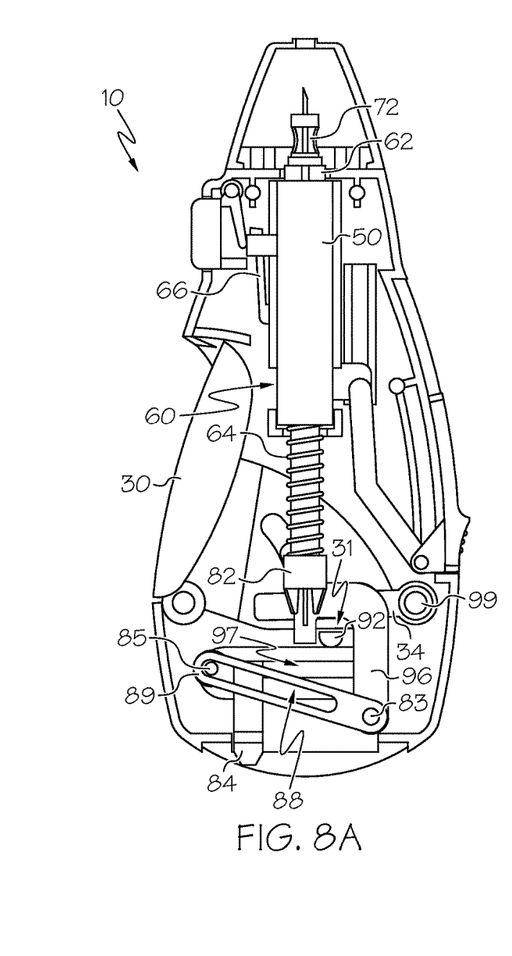
Figure 8B:
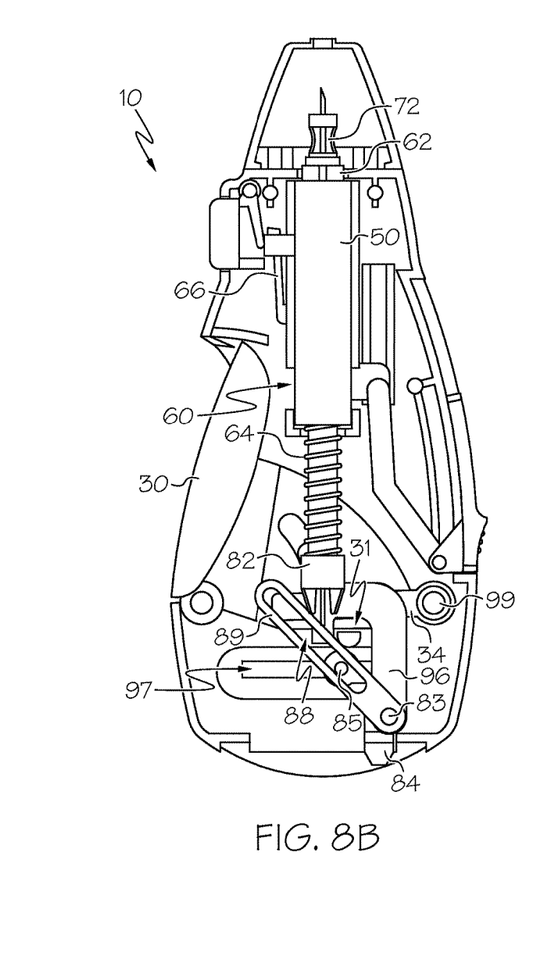

FIGS. 7A-12B show the operation of the lancing device throughout the lancing procedure with the positioning tab 84 of the tether 80 positioned in both the minimum (FIGS. 7A, 8A, 9A, 10A, 11A and 12A) and the maximum (FIGS. 7B, 8B, 9B, 10B, 11B and 12B) depth penetration settings. As shown in FIGS. 7A-7B, in a neutral position, the pivoting link 86 is angled such that the free end 80 is angled toward the housing distal end 24 and the pivot link pivoting aperture 86 is angled toward the housing proximal end 26. The elongated channel 88 extends along the same axis as the pivot link. It will be understood that the positioning tab 84 can be positioned at one or more intermediate points between the minimum depth and maximum depth settings as well. As the positioning tab 84 is repositioned from the minimum depth setting to the maximum depth setting, the pivot post 85 engages the elongated channel 88 and forces the angle of the pivot link to increase away from horizontal and push the free end 89 further toward the housing distal end 24.

As depicted, the lancet carrier 60 translates from a neutral position (FIGS. 7A, 7B), through a charging position (FIGS. 8A, 8B) to a charged position (FIGS. 9A, 9B) by actuating the charging handle 30 to energize the biasing spring 64 and engage the release finger 66 with the catch surface 54 of the drive core 50. Upon actuating the release member 40 to disengage the release finger 66 from the catch surface 54, the biasing spring propels the lancet carrier 60 along an advancing portion of the lancing stroke from the charged position within the housing to an advanced position (FIGS. 10A, 10B) wherein at least the sharp lancet tip 74 projects externally of the housing to penetrate the subject's skin at a lancing site.

Figure 11A:
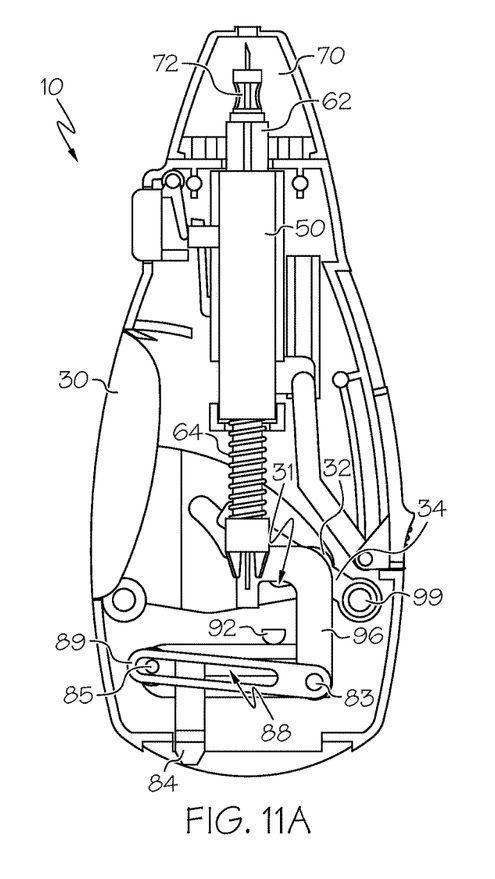
Figure 11B:
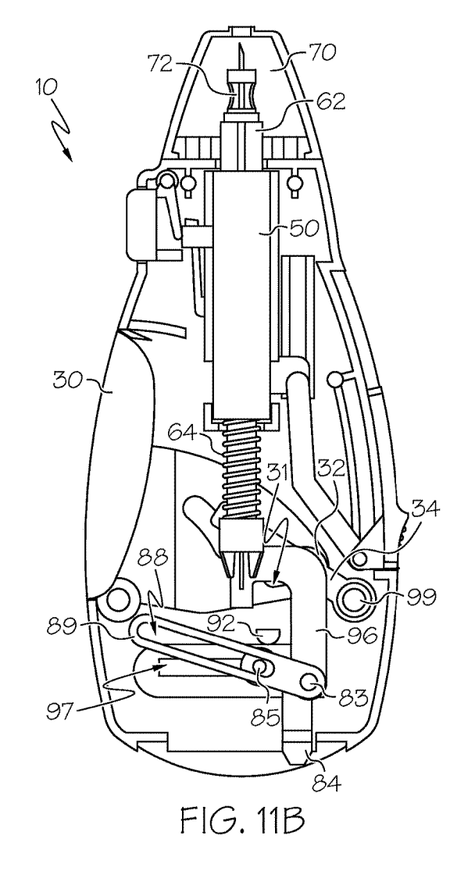

As depicted, the depth or extension of the lancet tip 74 projecting external to the housing is determined by the horizontal position of the pivot position post 85 relative to the engagement post 92. When driven forward by the bias spring 64, the pivot link pivot aperture 86 is pulled forward by the tether arm post 83. The maximum length between the pivot post 85 and engagement post 92 results in minimum depth penetration of the lancet 72 (FIG. 10A) because the pivot link engages the engagement post 92 with the pivot aperture 86 positioned proximally behind the engagement post. The minimum length between the pivot post 85 and the engagement post 92 results in maximum depth penetration of the lancet (FIG. 10B) because the pivot link engages the engagement post 92 with the pivot aperture 86 further toward the housing distal end 24 with respect to the engagement post. After the forward lancing stroke, the biasing spring 64 subsequently returns the lancet carrier 60 and the lancet 72 to the neutral position (FIGS. 11A, 11B).

Figure 12A:
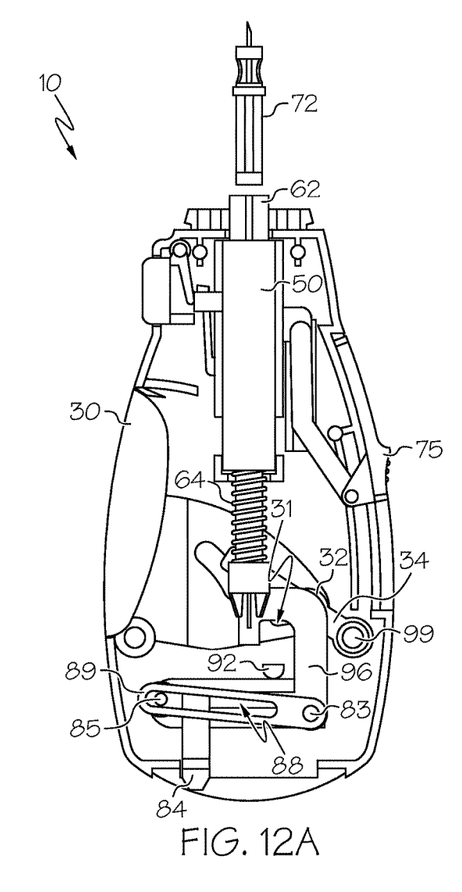
Figure 12B:
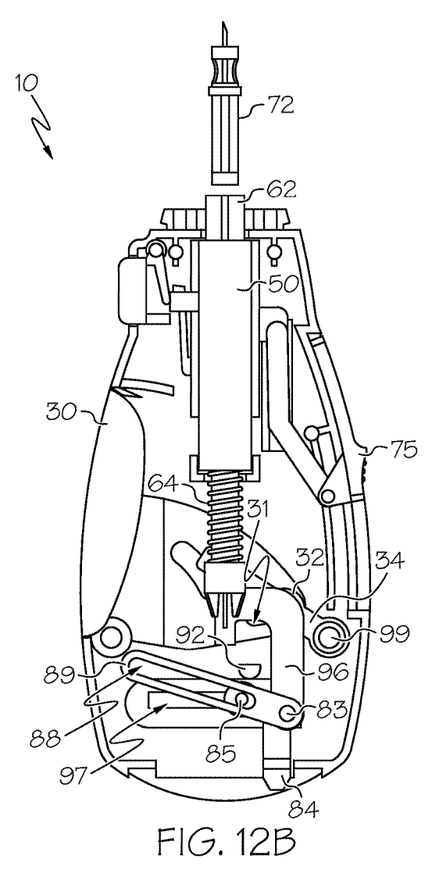

Optionally, the housing 20 comprises a removable endcap or nose-cone portion 70. As best shown in FIGS. 12A-12B, removal of the endcap 70 allows access for removal and replacement of the lancet 72 after use, for example by actuation of an ejector handle 75. In example embodiments, the ejector handle 75 movably mounts within an elongated opening 76 of the housing generally opposite the charging handle 30 and extends within the housing to selectively engage and eject the lancet.

Optionally, one or more releasable index detents (not shown) can be provided between the positioning tab 84 and the housing 20 to secure the positioning tab in a user-selected position within the elongated opening 81 on the housing or other portion of the lancing device, to permit indexed movement; or alternatively a continuously variable positional adjustment is provided. Example engagement features can include rigid points or a lip corresponding with cut-outs or notches in the surface of the opening 81, rubberized friction pads, or similar gripping elements.

While the invention has been described with reference to preferred and example embodiments, it will be understood by those skilled in the art that a variety of modifications, additions and deletions are within the scope of the invention, as defined by the following claims.

What is claimed is:

1. A depth-control mechanism for selectively-adjusting a lancing stroke depth of a lancet carrier, the depth-control mechanism comprising:
   a fixed engagement post;
   a positioning tab configured to be repositioned by a user relative to the engagement post along an axis orthogonal to the lancing stroke axis of the lancet carrier, wherein a first position of the positioning tab along the orthogonal axis corresponds to a first lancing stroke depth and a second position of the positioning tab along the orthogonal axis corresponds to a second lancing stroke depth, and
   a tether pivotally coupled between the positioning tab and the lancet carrier, the tether having a pivot axis relative to the axis orthogonal to the lancing stoke axis of the lancet carrier, wherein the tether is configured to engage the engagement post at a position on the tether, wherein the pivot axis is adjustable, wherein the positioning tab is configured to manipulate the adjustable pivot axis of the tether to change the position where the engagement post engages the tether and adjust the lancing stroke length of the lancet carrier.

2. The depth-control mechanism of claim 1, wherein the positioning tab is configured to be slidably repositioned along the axis orthogonal to the lancing stroke axis of the lancet carrier.

3. The depth-control mechanism of claim 1, wherein the tether comprises a pivot link comprising an elongated channel with an elongated axis extending between a minimum depth end and a maximum depth end.

4. The depth-control mechanism of claim 3, wherein the positioning tab is slidably secured in the pivot link elongated channel to move between the minimum depth end and the maximum depth end.

5. The depth-control mechanism of claim 3, wherein the elongated channel elongated axis is configured to pivot to at least two distinct angles with respect to the lancing stroke axis.

6. The depth-control mechanism of claim 5, wherein the positioning tab comprises a pivot post, the pivot link elongated channel configured to pivot to the at least two distinct axial angles about the pivot post.

7. The depth-control mechanism of claim 3, wherein the tether comprises an arm with a distal end secured to the lancet carrier and a proximal end pivotally secured to the pivot link.

8. The depth-control mechanism of claim 7, wherein the pivot link comprises a pivot aperture at the maximum depth end, and the arm comprises a pivot insert at the proximal end, the pivot insert pivotally inserted through the pivot link aperture.

9. The depth-control mechanism of claim 8, wherein the pivot link is configured to pivot around the arm pivot insert when the positioning tab is slidably repositioned with respect to the lancing stroke axis of the lancet carrier.

10. A depth-control mechanism for a lancing device comprising a housing having an upper housing shell and a lower housing shell, a drive-mechanism and a lancet carrier, translationally secured along a lancing stroke axis within a housing, the housing comprising an engagement post extending directly from the lower housing shell and a proximal elongated aperture, the depth-control mechanism comprising,
   a repositioning post slidably secured along the housing proximal elongated aperture, the repositioning post being distance-adjustable relative to the engagement post along an axis orthogonal to a lancing stroke axis of the lancet carrier wherein the entire repositioning post is able to move along an axis orthogonal to the lancing stroke axis; and
   a link coupling the repositioning post and the lancet carrier, the link comprising an elongate slot therein to slidably receive the repositioning post therein;
   wherein a distance between the engagement post and the repositioning post is adjustable to control the penetration depth of the lancet carrier lancing stroke; and
   wherein the link is configured to directly engage the engagement post.

11. The depth-control mechanism of claim 10, wherein the link elongate slot comprises a longitudinal axis extending between a minimum-depth end and a maximum-depth end, the elongate slot longitudinal axis configured to pivot to at least two distinct angles with respect to the lancing stroke axis.

12. The depth-control mechanism of claim 11, wherein the link comprises a pivot linkage comprising a pivot end and a free end, the pivot end comprising a pivot aperture and the pivot linkage comprising the link elongated slot extending between the pivot aperture and the free end.

13. The depth-control mechanism of claim 12, wherein the link comprises a pivot post pivotally inserted through the pivot linkage aperture.

14. The depth-control mechanism of claim 12, wherein the pivot linkage is configured to pivotally engage the housing engagement post to define the lancing stroke depth.

15. The depth-control mechanism of claim 10, wherein the distance between the repositioning post and the engagement post is inversely related to the lancing stroke depth.

* * * * *